United States Patent
Keintzel et al.

(10) Patent No.: US 10,228,333 B2
(45) Date of Patent: Mar. 12, 2019

(54) METHOD AND DEVICE FOR MEASURING THE SPEED OF A ROLLING STOCK

(75) Inventors: Georg Keintzel, Steyregg (AT); Günther Winter, Neunkirchen/Brand (DE)

(73) Assignee: PRIMETALS TECHNOLOGIES AUSTRIA GMBH (AT)

( * ) Notice: Subject to any disclaimer, the term of this patent is extended or adjusted under 35 U.S.C. 154(b) by 1115 days.

(21) Appl. No.: 13/996,569

(22) PCT Filed: Nov. 16, 2011

(86) PCT No.: PCT/EP2011/070191
§ 371 (c)(1),
(2), (4) Date: Jul. 31, 2013

(87) PCT Pub. No.: WO2012/084344
PCT Pub. Date: Jun. 28, 2012

(65) Prior Publication Data
US 2013/0307563 A1    Nov. 21, 2013

(30) Foreign Application Priority Data
Dec. 21, 2010    (EP) .................................... 10196184

(51) Int. Cl.
*G01N 22/00*    (2006.01)
*B21C 51/00*    (2006.01)
(Continued)

(52) U.S. Cl.
CPC ............. *G01N 22/00* (2013.01); *B21C 51/00* (2013.01); *G01P 3/44* (2013.01); *B21B 38/00* (2013.01); *B21B 2275/06* (2013.01)

(58) Field of Classification Search
CPC ............ G01P 3/44; G01N 22/00; B21C 51/00; B21B 38/00; B21B 2275/06
See application file for complete search history.

(56) References Cited

U.S. PATENT DOCUMENTS

| 3,824,015 A | * | 7/1974 | Petit | ......................... B21B 38/00 356/28 |
| 5,145,560 A | * | 9/1992 | Grenlulnd | ............ D21G 9/0027 162/198 |

(Continued)

FOREIGN PATENT DOCUMENTS

| CA | 2546634 A1 * | 11/2007 | ............. G01F 1/663 |
| CN | 101320086 A | 12/2008 | |

(Continued)

OTHER PUBLICATIONS

Russian Federation Office Action, dated Jul. 9, 2015, issued in corresponding Russian Federation Patent Application No. 2013133969/02(050817). Total 12 pages.
(Continued)

*Primary Examiner* — Huy Q Phan
*Assistant Examiner* — Adam Clarke
(74) *Attorney, Agent, or Firm* — Ostrolenk Faber LLP

(57) ABSTRACT

A method is disclosed for determining the speed of a rolling stock, for example the belt speed of a rolling belt, wherein electromagnetic radiation in the microwave range is transmitted to the rolling stock by at least one transmitting and receiving device and the belt speed is determined on the basis of the reflected and received reflection signal in an evaluation device. A device for carrying out such method is also disclosed.

19 Claims, 4 Drawing Sheets

(51) Int. Cl.
*G01P 3/44* (2006.01)
*B21B 38/00* (2006.01)

(56) References Cited

U.S. PATENT DOCUMENTS

| | | | |
|---|---|---|---|
| 2001/0046042 A1* | 11/2001 | Theile | G01P 3/803 |
| | | | 356/28 |
| 2002/0085201 A1* | 7/2002 | Shakespeare | G01N 21/89 |
| | | | 356/429 |
| 2002/0177972 A1* | 11/2002 | Riches | B21B 37/52 |
| | | | 702/142 |
| 2003/0034912 A1* | 2/2003 | Williams | G01S 13/56 |
| | | | 342/28 |
| 2006/0015288 A1 | 1/2006 | Ai et al. | |
| 2006/0096727 A1* | 5/2006 | Ferm | D21G 9/0027 |
| | | | 162/198 |
| 2008/0137062 A1* | 6/2008 | Holton | G01P 3/366 |
| | | | 356/28 |
| 2009/0294670 A1* | 12/2009 | Tsuji | G01N 22/00 |
| | | | 250/338.1 |
| 2010/0188500 A1* | 7/2010 | Bouchard | G01N 21/8986 |
| | | | 348/93 |
| 2012/0085171 A1* | 4/2012 | Park | G01S 17/58 |
| | | | 73/521 |
| 2012/0303315 A1* | 11/2012 | Della Vedova | G01P 1/026 |
| | | | 702/149 |
| 2013/0256275 A1* | 10/2013 | Watanabe | B21C 37/0826 |
| | | | 219/61 |

FOREIGN PATENT DOCUMENTS

| | | |
|---|---|---|
| DE | 3047728 | 7/1982 |
| DE | 4102248 | 7/1992 |
| DE | 10226499 A1 | 12/2003 |
| EP | 0 068 431 | 1/1983 |
| GB | 1 207 241 | 9/1970 |
| GB | 1 496 138 | 12/1977 |
| GB | 1 530 171 | 10/1978 |
| JP | 1-113102 | 5/1989 |
| JP | 2010-155273 A | 7/2010 |
| RU | 2 194 586 C2 | 12/2002 |
| SU | 168244 A | 11/1965 |

OTHER PUBLICATIONS

Chinese Office Action dated Jul. 3, 2014 corresponding to Chinese Application No. 201180061761.2 (12 pages).

International Search Report dated Feb. 16, 2012 in corresponding PCT International Application No. PCT/EP2011/070191, and English translation thereof.

R.L. Ricciatti et al., "Laser Velocimetry," AISE Steel Technology, vol. 73, No. 6, pp. 38-41, Jun. 1, 1996.

Russian Notice of Allowance dated Mar. 29, 2016 in corresponding Russian Patent Application No. 2013133969/02 (050817).

Indian Examination Report, dated Sep. 7, 2018, issued in corresponding Indian Patent Application No. 5178/DELNP/2013, including English translation within Examination Report. Total 6 pages.

* cited by examiner

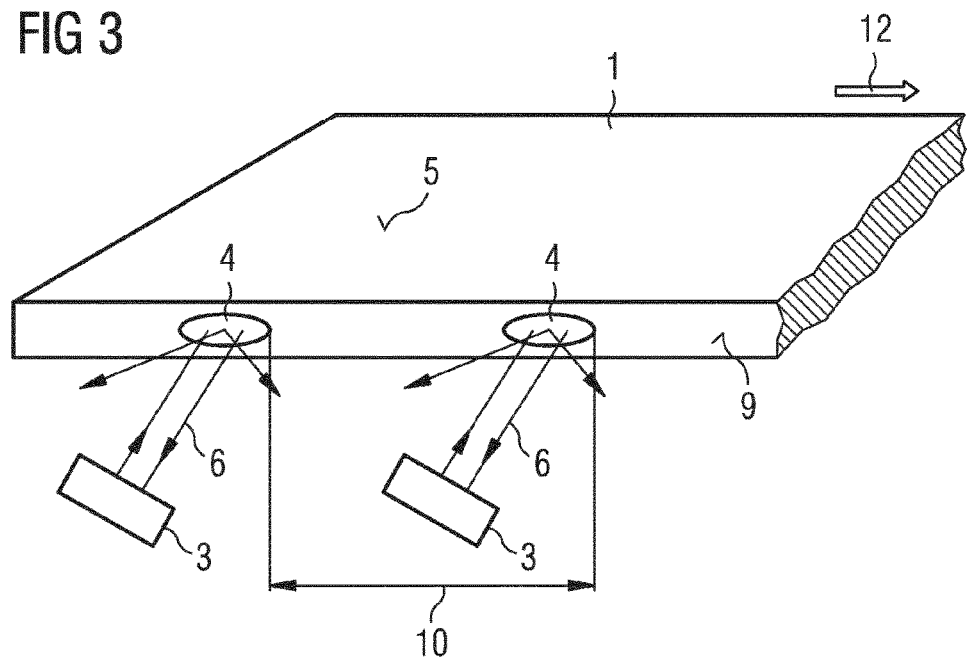
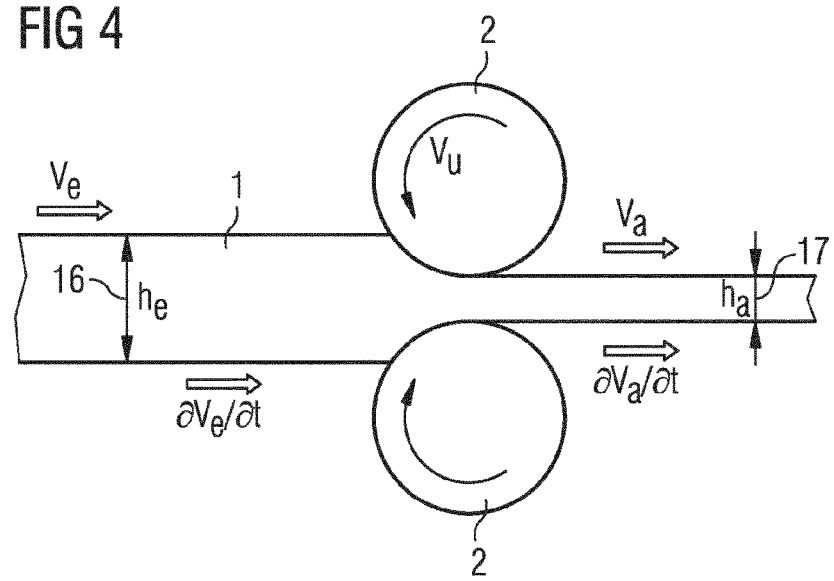

METHOD AND DEVICE FOR MEASURING THE SPEED OF A ROLLING STOCK

CROSS-REFERENCE TO RELATED APPLICATIONS

This application is a U.S. National Stage Application of International Application No. PCT/EP2011/070191 filed Nov. 16, 2011, which designates the United States of America, and claims priority to EP Patent Application No. 10196184.5 filed Dec. 21, 2010, the contents of which are hereby incorporated by reference in their entirety.

TECHNICAL FIELD

This disclosure relates to a method and a device for measuring the speed of a rolling stock, in particular the strip speed of a metal strip, wherein electromagnetic radiation in the microwave range and directed by means of a transmitting device onto the surface of the metal strip is transmitted and electromagnetic radiation reflected from there is received by means of a receiving device. The disclosure also relates to a method for activating a rolling system as well as to retrofitting a rolling system.

BACKGROUND

To be able to control or regulate the individual roll stands of a rolling train appropriately, reliable detection of the speed of the rolling stock is necessary.

To detect the speed of a metal strip the rotational movement of the working rollers of a roll stand or also of other rollers that are in contact with the rolling stock can be used for instance. However the problem which arises here is that the measurement signal must be corrected since slippage can occur in practice between working rollers or rollers and rolling stock respectively.

Non-contact measurement sensors for measuring the strip speed are known, such as for example from EP 1 252 942 A1. In such cases a laser beam is transmitted onto the train surface and the strip speed is determined from the Doppler shift of the reflected signal. Such an optical measurement system is however susceptible to faults. Since liquid coolant is needed for the cooling of working rollers, contact with the high-temperature of a hot strip results in the formation of steam. The propagation of the light beam is thus adversely affected and this results in inaccuracies in the speed measurement. Because of the harsh ambient conditions of a rolling train it can also occur that an optical measurement system fails completely.

A precise and reliable determination of the strip speed however also has other advantages, including the ability to determine the thickness of the metal strip in indirect ways from the strip speed, as is explained in more detail under FIG. 4.

SUMMARY

One embodiment provides a method for determining the speed of rolling stock, especially the strip speed of a rolling strip, wherein the electromagnetic radiation in the microwave range is transmitted onto the rolling stock with at least one transmitting and receiving device and the strip speed is determined in an evaluation device from the reflection signal thrown back and received.

In a further embodiment, at least two transmitting and receiving devices are used, by means of which electromagnetic radiation directed onto a reflector surface of the rolling stock is generated in each case, wherein the reflector surfaces lie at a distance from one another on a line running in parallel to the direction of movement, and from the portion thrown back from the respective reflector surface a reflection signal is formed in each case, wherein each of these reflection signals is supplied to an evaluation device, by means of which the strip speed is determined using a correlation method.

In a further embodiment, the reflector surfaces are each formed by a surface area of the narrow side of the rolling stock.

In a further embodiment, the reflection signal is formed by the timing curve of the backscatter amplitudes of the previously transmitted electromagnetic radiation.

In a further embodiment, the electromagnetic radiation is generated in a frequency range of 300 MHz to 300 GHz and is transmitted by means of an antenna with a directional effect directed onto the rolling stock.

Another embodiment provides a device for determining the speed of a rolling stock, in particular the strip speed of a rolling strip, comprising: at least one transmitting and receiving device which is configured to transmit electromagnetic radiation in the microwave range onto at least one reflector surface formed by a part of the surface of the rolling stock and to form a reflection signal from the electromagnetic radiation thrown back and received from the respective reflector surface; and an evaluation device, to which the reflection signal is supplied via a signal line and which is configured to determine the strip speed from said signal.

In a further embodiment, the device includes two transmitting and receiving devices, which are configured to transmit electromagnetic radiation onto an assigned reflector surface in each case, whereby the reflector surfaces lie at a distance from one another on a line running in parallel to the direction of movement of the rolling stock, and to form a reflection signal in each case from the portion of the electromagnetic radiation thrown back from the respective reflector surface, wherein each of these reflection signals is supplied to the evaluation device which determines the strip speed using a correlation method.

In a further embodiment, the transmitted electromagnetic radiation is directed onto a side surface of the rolling strip.

In a further embodiment, each reflection signal is formed by the temporal curve of the backscatter amplitudes of the previously transmitted electromagnetic radiation.

In a further embodiment, the transmitting and receiving device has a transmitter and receiver antenna which is embodied as an aperture radiator, which has a club-shaped directional characteristic.

In a further embodiment, the aperture radiator is a horn or a funnel radiator.

In a further embodiment, the aperture radiator is integrated into the stripper of a working roller of a roll stand.

In a further embodiment, the electromagnetic radiation directed at the rolling stock has a frequency ranging from 300 MHz to 300 GHz.

In a further embodiment, the aperture radiator is integrated into the lateral guide of a roll stand.

In a further embodiment, the aperture radiator is integrated from below into a transfer table close to the rolling gap of a roll stand.

In a further embodiment, the aperture radiator of a rolling stand is integrated into the loop lifter of a rolling train.

In a further embodiment, the aperture radiator of a rolling stand is mounted on the loop lifter of a rolling train, so that it measures laterally on the strip.

Another embodiment provides a method for controlling a rolling system for producing a rolling strip, wherein the rolling strip is fed in a direction of movement through the rolling gap of a pair of working rollers and when this is done the thickness of the rolling strip is reduced from an entry thickness to an exit thickness, wherein, for the purposes of a thickness regulation, an actual value of the entry thickness and/or of the exit thickness is supplied to a control system, wherein, for detecting the entry thickness and/or the exit thickness, any of the methods and/or devices disclosed above may be employed.

Another embodiment provides a method for retrofitting a rolling system for producing a rolling strip, wherein the rolling system has a number of roll stands and a control system for controlling the roll stands, wherein the rolling strip is guided in a direction of movement through the rolling gap of a pair of working rollers and during this process reduces the thickness of the rolling strip from an entry thickness to an exit thickness, wherein, for the purposes of thickness regulation a measured actual value of the entry thickness and/or of the exit thickness is supplied to the control system, any of the methods and/or devices disclosed above may be employed.

BRIEF DESCRIPTION OF THE DRAWINGS

Example Embodiments are Discussed Below with Reference to the Drawings, in Which:

FIG. 3 shows a perspective diagram of another exemplary embodiment of the invention with two transmitting and receiving devices arranged in series behind one another, which are arranged to the side of the rolling strip;

FIG. 4 shows a schematic diagram in which a rolling strip is shown engaging with two working rollers;

DETAILED DESCRIPTION

Figure 1:
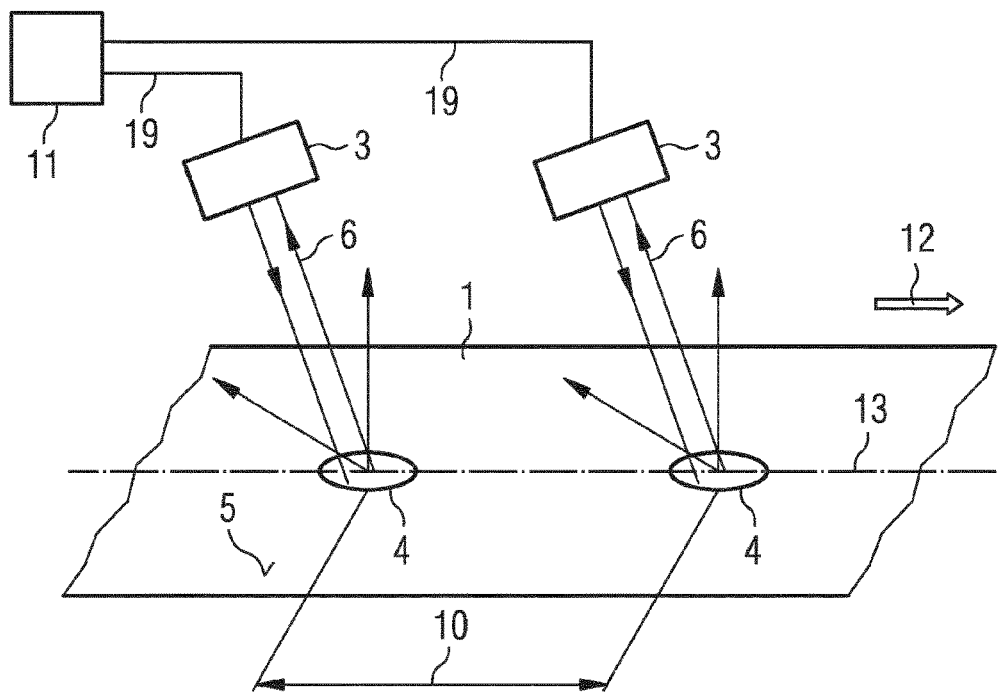
FIG. 1 shows a perspective diagram of an exemplary embodiment of the invention with two transmitting and receiving devices arranged in series behind one another, which each transmit electromagnetic radiation onto the width surface of a metal strip and receive the reflection signal.

Embodiments of the present invention provide a method and a device for determining the speed of a rolling stock, e.g., the strip speed of a metal strip, with improved accuracy and with greater reliability.

In accordance with at least some embodiments, electromagnetic radiation is transmitted with at least one transmitting and receiving device onto the rolling stock and the strip speed is determined in an evaluation device from the received reflection signal thrown back.

An embodiment with at least two transmitting and receiving devices which are arranged at a distance one behind the other in the direction of movement of the rolling stock and transmit high-frequency electromagnetic radiation in each case to an area of the surface (reflector surface) of the rolling stock is preferred. The frequency of this electromagnetic radiation in such cases can preferably lie in the range of 300 MHz to 300 GHz, especially in the range of radar waves. Because of the roughness or texture of the rolling strip surface this RF radiation is scattered and partly reflected back in the direction of the transmitter. A reflection signal is obtained in each case from this reflected radiation and is supplied to an evaluation device. The evaluation device uses a correlation function, i.e. the relationship between two or more reflection signals, to determine the strip speed. Cross-correlation can for example be used as the correlation function. The reflection signals can be evaluated by a digital signal processor, by the evaluation device being embodied as a computing device. In this computing device the at least two reflection signals are digitized and subsequently evaluated by a corresponding correlation algorithm. The radar radiation, which is longer-wave by comparison with light, makes it possible to determine the strip speed with a better accuracy, since steam and other contaminants in the propagation path of the electromagnetic radiation have a comparatively lower influence compared to light radiation. A radar measurement system is more robust by comparison with an optical measurement system. The installation space needed is comparatively small. The improved accuracy and availability of the inventive speed measurement enable the automation system of a rolling train to be simplified and at the same time the product accuracy to be improved. This is especially beneficial for example in the thickness regulation in rolling trains in a tandem arrangement such as for example in cold tandem trains or hot wide strip trains. Thickness errors such as previously occurred at the strip head can be reduced. The strip thickness can also be determined with high accuracy in the evaluation device using the strip speed.

It can be of advantage for the narrow side of the rolling stock rather than the wide side to be used as the reflector surface. This means that the disruptive influence of steam and contaminants in the beam path is lower. The measuring device can then be arranged to the side of the rolling stock where more space is available as a rule. Above and beyond this the advantage is produced of integration into a loop lifter or into a lateral guide of a rolling train being possible.

It can be especially simple in such cases if the temporal amplitude curve of the reflected radiation is used in each case for the correlation of the reflection signals.

It has proved to be advantageous for the reflector surface on the rolling stock to be kept small. With a predetermined space between the antenna and strip this allows the area of illumination on the metal strip to be kept small, which is advantageous for the correlation of the reflection signals.

It can be especially advantageous for the electromagnetic radiation to be emitted by a hollow conductor, the aperture of which is directed onto the surface of the rolling stock. An aperture radiator which has a club-shaped directional characteristic is advantageous.

In such cases it can be sensible, when the device is installed between roll stands, for the hollow conductor to be composed of straight or curved sections, so that the devices for generating and emitting the electromagnetic waves are spatially removed from one another. A corresponding embodiment of a horn radiator enables the illumination to be directed very explicitly to a desired area of the strip surface without the for example thermally-sensitive transmitter and receiver being located in a hazardous area, e.g. close to the surface of a hot strip, which usually has a temperature of 800 to 1000° C. The curved embodiment of the hollow conductor also makes it possible to integrate the speed measurement into other mechanical parts of the system such as into a loop lifter of a hot wide strip train for example.

In one embodiment the aperture radiator is integrated into the stripper of a working roller of a roll stand or into the transfer table close to the rolling gap. This means that the strip speed is measured in the immediate vicinity of the rolling gap of a roll stand and it is possible to significantly reduce the dead time of a thickness regulation.

FIG. 1 shows a first exemplary embodiment of the invention.

Two transmitting and receiving devices 3 arranged at a distance from one another can be seen. Each of these transmitting and receiving devices 3 in this case continually generates bundled microwave radiation. This radio-frequency radiation (radar waves) is supplied to an aperture radiator not shown in any greater detail in FIG. 1, the free opening of which points towards the metal strip 1. The aperture radiator transmits electromagnetic waves 6 at a specific spatial angle onto a width surface 5 of the metal strip 1. The microwave radiation is scattered diffusely on the strip surface 5. Depending on the reflection behavior, a proportion of this electromagnetic radiation 6 is reflected back from the respective reflector surface 4 to the transmitting and receiving device 3. The microwave radiation thrown back is received with a receive antenna not shown in any greater detail. From the portion thrown back a reflection signal is generated in each of the two transmitting and receiving devices 3. The two reflection signals are supplied via signal lines 19 to an evaluation device 11. Signal analysis is undertaken in the evaluation device 11. The evaluation device 11 determines from the supplied reflection signals, by cross correlation of the amplitude curves 7, 8 (FIG. 2), the speed of the metal strip 1. Since electromagnetic waves in the microwave radar range are relatively insensitive with regard to steam and other disruptive influences, the strip speed can be determined with a very high accuracy. With hot wide strip trains in particular this is of particular advantage. The measurement system is robust and largely immune to faults.

As shown in the diagram of FIG. 1, the transmission and receiving of the microwave radiation occurs at a specific spatial angle in relation to the plane predetermined by the width surface 5 of the metal strip 1. The reflector surfaces 4 lie at a distance 10 from one another and in each case on a line 13 which runs in parallel to the direction of movement 12 of the metal strip 1. The end result of this is that the reflection amplitudes in the timing curve are very similar and the strip speed can be determined with good accuracy.

Figure 2:
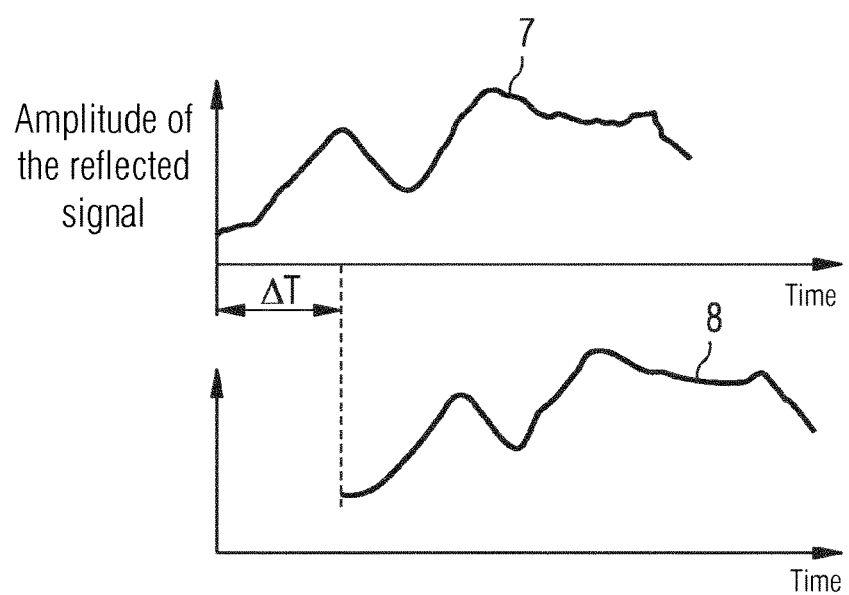
FIG. 2 shows a timing curve of the two reflection signals of FIG. 1.

FIG. 2 shows the amplitude (backscatter amplitudes) of the two reflection signals 7 and 8 determined by the properties of the surface of the rolled strip along the line 13 as a function of the time. As stated, the reflector surfaces 4 lie in a line 13 parallel to the direction of movement 12 of the metal strip 1 and at a distance 10 from one another, so that the same surface section runs below the two transmitting and receiving devices 3 offset in time. The result of this is that the two reflection signals 7, 8 are very similar in their time curve. As can be seen from the diagram of FIG. 2, the two reflection signals 7, 8 are offset in time by $\Delta T$ in relation to one another. The correlation of the two reflection signals 7 and 8 becomes maximum if the time shift up reaches the quotient of the distance between the two transmitting and receiving devices 3 and the current strip speed, in other words when a reflection area 4 is measured with the first receiver 3 by the spatially distant second receiver 3. Since the distance 10 between the two reflector surfaces 4 is known, the strip speed can be calculated with high accuracy from this measurement arrangement.

FIG. 3 shows another exemplary embodiment of the invention in which it is not the width surface 5 of the rolling strip 1, but a side surface 9 which is used as the reflection area 4 for the electromagnetic radiation 6. Here too the reflector surfaces 4 illuminated with electromagnetic radiation by the two transmitting and receiving devices 3 are arranged at a distance 10 apart from one another in the direction of movement 12 of the metal strip 1. Likewise the two reflector surfaces 4 lie on a line 13 which again runs in parallel to the direction of movement 12 of the rolling strip 1.

FIG. 4 shows a rolling strip 1 which is being reduced by the pressure of two working rollers 2 from an entry thickness 16 to an exit thickness 17. Predetermined by the continuity of the mass flow, the result of the thickness reduction is that the strip speed $v_e$ on entry into the rolling gap, the roller circumferential speed $v_u$ and the strip speed $v_a$ on exit from the rolling gap differ. The precise knowledge of the strip speed is of great importance for the regulation of a mostly multi-stand rolling system. In addition if one of the strip thicknesses (entry thickness $h_e$ or exit thickness $h_a$) and the speed $v_e$ on entry into a roll stand and speed $v_a$ on exit from a roll stand are known, the other strip thickness can be determined (assuming entry strip width $b_e$=exit strip width $b_a$). The following equation applies:

$$\partial v_e/\partial t = \partial v_a/\partial t$$

$$h_e * b_e * v_e = h_a * b_a * v_a$$

It goes without saying that instead of two, a plurality of such transmitting and receiving devices 3 can also be arranged spaced from one another in the direction of movement 12 of the strip. The signal analysis of a plurality of backscatter amplitudes makes it possible that disruptive influencing variables of the strip movement which lie transverse to the movement direction (rolling direction) can be compensated for. The radar transmitting device and the radar receiving device can be implemented into two spatially separated devices or into a single device. This also applies in a similar manner for the evaluation device 11 and the transmitting and receiving device 3.

The distance between the transmitting and receiving devices 3 and a hot strip is on the one hand selected to be sufficiently large in the examples shown in FIG. 1 or FIG. 3 for mechanical or thermal damage to the measurement device to be excluded. On the other hand the distance is selected so that the electromagnetic radiation emitted by the antennas or aperture radiators illuminates as small a surface area as possible on the surface of the metal strip. This enables the correlation between the two measurement positions to be better evaluated.

A concentration of the electromagnetic radiation on an especially small illumination surface on the strip surface can be achieved by microwave antennas, which has a strongly bundled directional characteristic. An especially good bundling of the electromagnetic radiation can in particular be achieved by aperture radiators, such as horn or funnel radiators, with a club-shaped directional characteristic.

Figure 5:
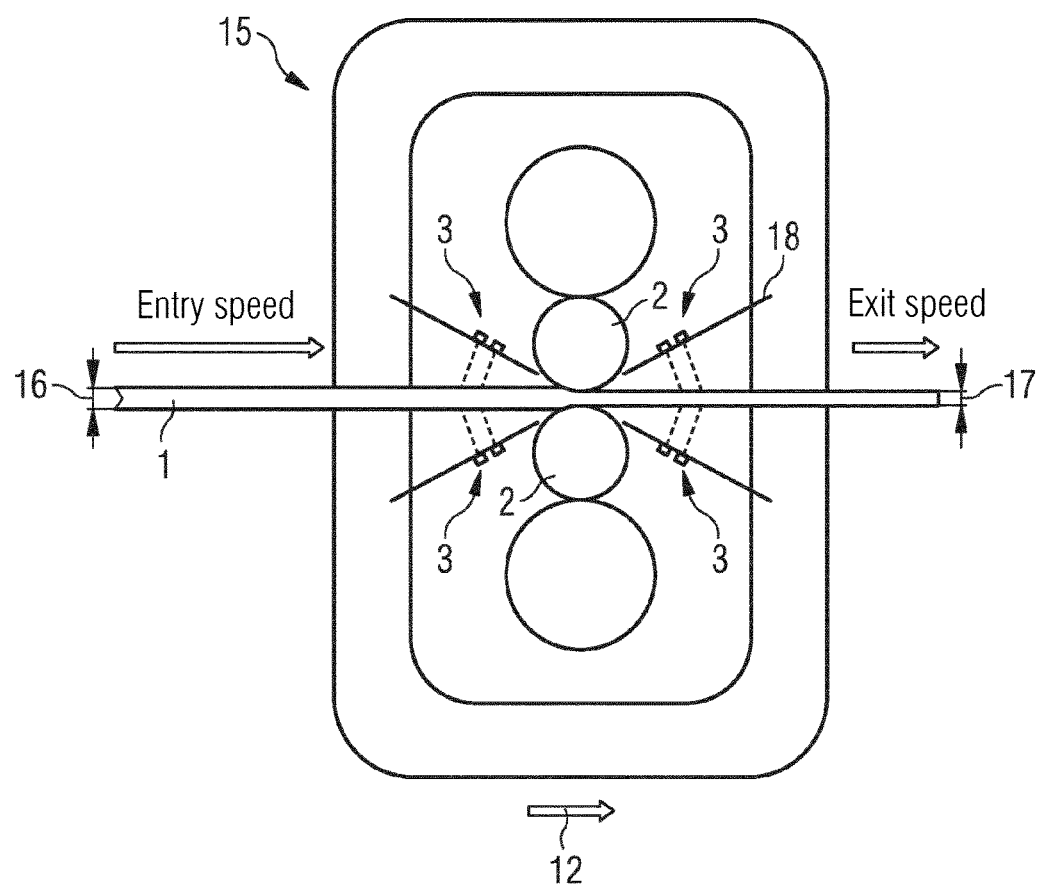
FIG. 5 shows a schematic diagram of a roll stand, seen from the side.

FIG. 5 shows a greatly simplified diagram of a roll stand 15 seen from the side. The rolling stock 1 is reduced from the entry thickness 16 in the gap between the working rollers 2 to the exit thickness 17. The transmitter and receiver antennas of the radar unit 3 are built into the stripper 18. This installation in the roll stand or in the roll stands 15 respectively has the advantage of a shorter distance to the rolling gap, i.e. the regulation circuit of the thickness regulation has no dead time. In the exemplary embodiment shown this type of transmitting and receiving device 3 is arranged both on the entry side and also on the exit side on the upper side and on the lower side of the rolling strip 1 respectively. These radar measurement devices 3 can be attached both in the middle of the rolling line and also off center. It can also be advantageous for a number of these radar measurement devices 3 to be built into one roll stand 15 for reasons of redundancy both on the entry side and also on the exit side.

Figure 6:
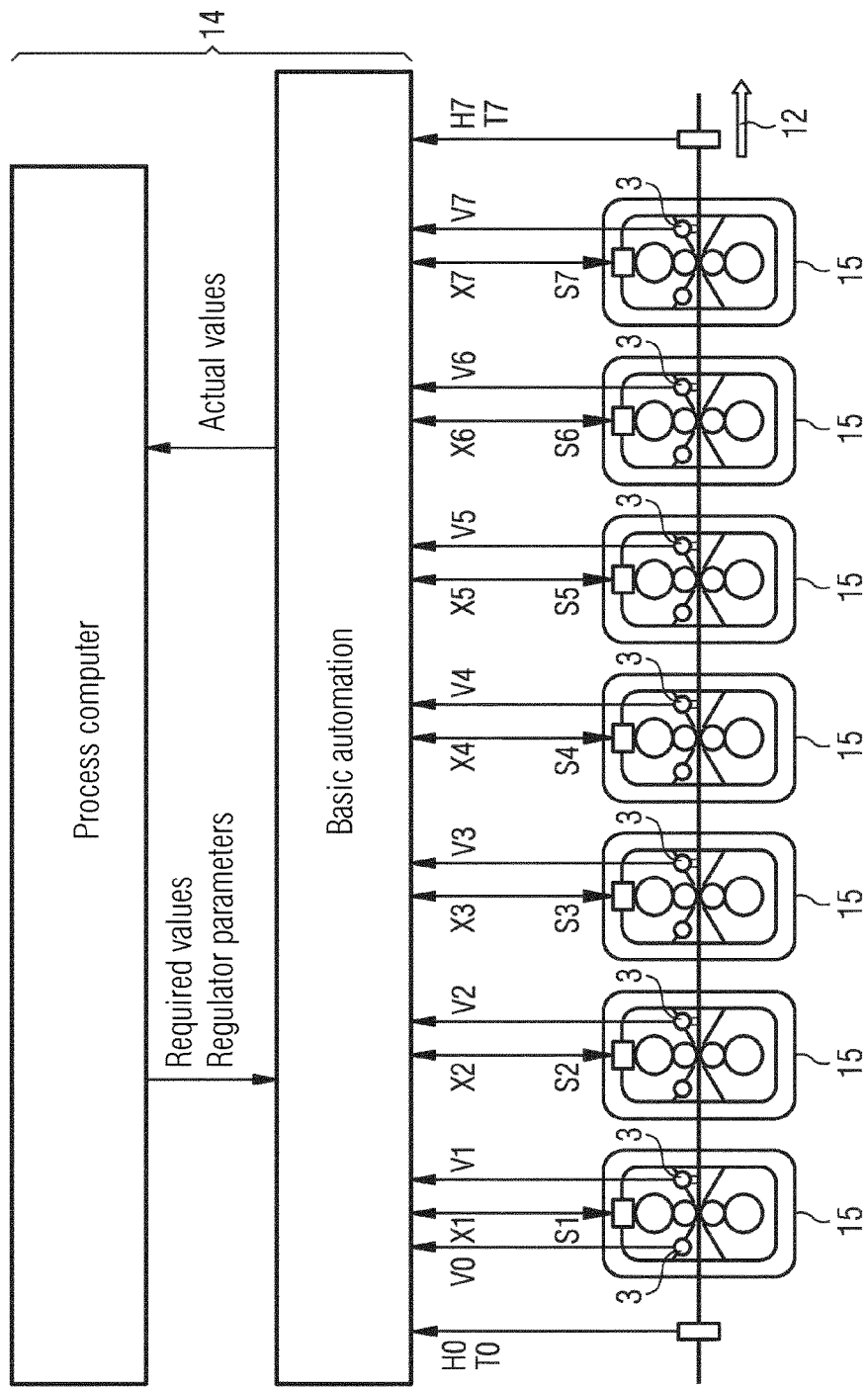
FIG. 6 shows a simplified block diagram for control of a rolling system.

FIG. 6 shows a simplified block diagram of the automation of a rolling system. The individual roll stands 15 in this case are connected via signal lines to a control system 14. This control system 14 may include a process computer and a basic automation system (level 1/level 2 automation). The process computer in this case provides the basic automation with the setpoint values and parameters for the regulation or control respectively. The basic automation supplies the process computer with actual values from the process. Transmitting and receiving devices 3 are installed on each roll stand 15, which deliver radar measured values of the strip speed V0 to V7 to the higher-ranking basic automation. These radar strip speed measured values V0 to V7 are used for thickness regulation. This radar strip speed measurement enables evaluation of the otherwise normal speed sensors on the main drives of the roll stands to be dispensed with. In FIG. 6 the transmission of further measured values/setpoint values between roll stands 15 and higher-ranking control system 14 is shown in the diagram; Ho, H7 strip thickness; T0, T7 temperature; X1, X7 rolling force, bending forces; adjustment positions, looper position etc. and also S1-S7 adjustment position, bending forces, speed etc.

Another embodiment of the invention can lie in a method for controlling a rolling system for producing a rolling strip, wherein the rolling strip is guided in a direction of movement through the rolling gap of a pair of working rollers. In this case the rolling strip undergoes a thickness reduction from an entry thickness 16 to an exit thickness 17. For purposes of controlling the thickness a control system 14 is supplied with one or more actual values of the entry thickness 16 and/or the exit thickness 17. In the detection of the entry thickness 16 and/or the exit thickness 17 a method or a device is employed.

A further embodiment of the invention can lie in retrofitting the system to an existing rolling system for producing a rolling strip.

LIST OF REFERENCE CHARACTERS USED

1 Rolling strip
2 Working roller
3 Transmitting and receiving device
4 Reflector surface
5 Width surface of the rolling strip
6 Electromagnetic radiation
7 Backscatter amplitude of the first transmitting and receiving device
8 Backscatter amplitude of the second transmitting and receiving device
9 Side surface of the rolling strip
10 Distance between the reflector surfaces
11 Evaluation device
12 Direction of movement of the rolling strip
13 Line
14 Control system
15 Roll stand
16 Entry thickness
17 Exit thickness
18 Stripper
19 Signal line

What is claimed is:

1. A method for determining a single value of the strip speed of a metal rolling strip along a direction of movement, comprising:
   using at least two transmitting and receiving devices to:
      generate and direct electromagnetic radiation in the microwave range onto at least two reflector surfaces of the metal rolling strip, wherein the reflector surfaces lie at a distance from one another on a line parallel to the direction of movement, and
      for each reflector surface, determining a reflection signal corresponding to a portion of the electromagnetic radiation reflected by that reflector surface, and
   using an evaluation device to determine a single value of the strip speed based on the determined reflection signals using a correlation method.

2. The method of claim 1, wherein each reflector surface comprises a surface area of a narrow side of the metal rolling strip.

3. The method of claim 1, wherein the reflection signal is detected from a timing curve of backscatter amplitudes of the transmitted electromagnetic radiation.

4. The method of claim 1, wherein the electromagnetic radiation is generated in a frequency range of 300 MHz to 300 GHz, and transmitted by an antenna with a directional effect directed onto the metal rolling strip.

5. The method of claim 1, wherein the portion of the electromagnetic radiation reflected by that reflector surface is electromagnetic radiation in the microwave range.

6. The method of claim 1, wherein the correlation method is based on a time shift between the determined reflection signals.

7. A device for determining a single value of a strip speed of a metal rolling strip along a direction of movement, the device comprising:
   at least two transmitting and receiving devices, each configured to:
      transmit electromagnetic radiation in the microwave range onto a respective assigned reflector surface of the metal rolling strip, wherein the reflector surfaces lie at a distance from one another on a line parallel to the direction of movement, and
      determine a reflection signal from a portion of the electromagnetic radiation reflected by a respective reflector surface, and
   an evaluation device configured to determine a single value of the strip speed of the metal rolling strip based on the determined reflection signals using a correlation method.

8. The device of claim 7, wherein each transmitting and receiving device has a transmitter and receiver antenna embodied as an aperture radiator having a club-shaped directional characteristic.

9. The device of claim 8, wherein the aperture radiator is a horn or a funnel radiator.

10. The device of claim 8, wherein the aperture radiator is integrated into a stripper of a working roller of a roll stand.

11. The device of claim 8, wherein the aperture radiator is integrated into a lateral guide of a roll stand.

12. The device of claim 8, wherein the aperture radiator is integrated from below into a transfer table close to a rolling gap of a roll stand.

13. The device of claim 8, wherein the aperture radiator of a rolling stand is integrated into a loop lifter of a rolling train.

14. The device of claim 8, wherein the aperture radiator of a rolling stand is mounted on a loop lifter of a rolling train, such that it measures laterally on the metal rolling strip.

15. The device of claim 7, wherein the transmitted electromagnetic radiation is directed onto a side surface of the metal rolling strip.

16. The device of claim 7, wherein each reflection signal is formed by the temporal curve of the backscatter amplitudes of the previously transmitted electromagnetic radiation.

17. The device of claim 7, wherein the electromagnetic radiation directed at the metal rolling strip has a frequency ranging from 300 MHz to 300 GHz.

18. The device of claim 7, wherein the correlation method is based on a time shift between the determined reflection signals.

19. The device of claim 7, wherein the portion of the electromagnetic radiation reflected by the respective reflector surface is electromagnetic radiation in the microwave range.

* * * * *